(12) United States Patent
Xie et al.

(10) Patent No.: US 9,421,181 B2
(45) Date of Patent: Aug. 23, 2016

(54) ANTIHYPOXIC PHARMACEUTICAL COMPOSITION AND APPLICATION THEREOF

(71) Applicant: CHANGZHOU HI-TECH DISTRICT MULTIPLE DIMENSION INDUSTRY TECHNOLOGY INSTITUTE CO., LTD, Jiangsu (CN)

(72) Inventors: Hebing Xie, Jiangsu (CN); Qingyi Li, Jiangsu (CN); Shuhua Gu, Jiangsu (CN); Weihong Lv, Jiangsu (CN)

(*) Notice: Subject to any disclaimer, the term of this patent is extended or adjusted under 35 U.S.C. 154(b) by 0 days.

(21) Appl. No.: 14/889,594

(22) PCT Filed: Apr. 21, 2014

(86) PCT No.: PCT/CN2014/075770
§ 371 (c)(1),
(2) Date: Nov. 6, 2015

(87) PCT Pub. No.: WO2014/180238
PCT Pub. Date: Nov. 13, 2014

(65) Prior Publication Data
US 2016/0081966 A1 Mar. 24, 2016

(30) Foreign Application Priority Data
May 6, 2013 (CN) .......................... 2013 1 0162336

(51) Int. Cl.
*A61K 31/497* (2006.01)
*A61K 31/205* (2006.01)
*A61K 31/4375* (2006.01)
*A61K 31/495* (2006.01)

(52) U.S. Cl.
CPC ........... *A61K 31/205* (2013.01); *A61K 31/4375* (2013.01); *A61K 31/495* (2013.01)

(58) Field of Classification Search
None
See application file for complete search history.

(56) References Cited

U.S. PATENT DOCUMENTS 6,572,899 B1 * 6/2003 Gorsek ................ A61K 31/122 424/725
6,964,969 B2 * 11/2005 McCleary .............. A61K 31/00 424/752

FOREIGN PATENT DOCUMENTS

CN 1723896 A 1/2006
CN 101356972 A 2/2009

OTHER PUBLICATIONS

English translation of Written Opinion of the International Search Authority (ISA/CN); Jul. 23, 2014; four pages.

* cited by examiner

*Primary Examiner* — Heidi Reese
(74) *Attorney, Agent, or Firm* — John A. Fortkort; Fortkort & Houston PC

(57) ABSTRACT

The present invention discloses an antihypoxic pharmaceutical composition and application thereof. The pharmaceutical composition contains vinpocetine and L-carnitine or a derivative thereof and a pharmaceutically acceptable salt thereof, and also can contain trimetazidine or a pharmaceutically acceptable salt thereof.

22 Claims, No Drawings

ANTIHYPOXIC PHARMACEUTICAL COMPOSITION AND APPLICATION THEREOF

CROSS-REFERENCE TO RELATED APPLICATIONS

This application is a 371 PCT national application claiming priority to PCT/CN2014/075770, filed Apr. 21, 2014, having the same title, and the same inventors, and which is incorporated herein by reference in its entirety; which application claims the benefit of priority from Chinese application number 201310162336.3, filed May 6, 2013, having the same title, and the same inventors, now pending, and which is incorporated herein by reference in its entirety.

TECHNICAL FIELD

The present invention relates to pharmaceutical field, and specifically involves an antihypoxic pharmaceutical composition and application thereof for diseases and illnesses caused by hypoxia.

BACKGROUND ART

Hypoxia refers to a pathological process in which the metabolism, function and morphological structure of the tissue are abnormally changed due to lack of oxygen supply or oxygen impairment. Such pathologies as shock, respiratory dysfunction, cardiac insufficiency and anemia, etc. could impair organs vital to life like brain and heart and even cause people to die. Hypoxia is also common in environmentally-affected pathological process. High-altitude flight, diving and work in severe hypoxic environment such as plateau, air-tight cabin or tunnels will directly influence human activities and even threat their lives. Therefore, it is of great social significance to study and develop antihypoxic drugs.

Hypoxia could slow down the aerobic metabolism of the tissues all over the body. It is indicated by many researches that mitochondria damage may be the core of energy metabolism dysfunction for cell after hypoxia. In the circumstance of hypoxia, large numbers of free radicals are produced by the organism. Mitochondria, the main producer for endogenous free radical, are the target of free radicals. Oxygen free radicals produced after hypoxia can make toxic reaction to biomacromolecule, mainly reflecting in lipid peroxidation, which can cause abnormal membrane structure and dysfunction. The fluidity of mitochondria decreases after they are impaired by free radicals, thus decreasing the function of the mitochondria and slowing down the activity of the enzyme in the membrane. The degradation of mitochondrial membrane phospholipids can lead to damage to mitochondria, which will influence the activity of cytochrome c-oxidase and ATP synthase, decreasing the synthesis of ATP and directly cause cell impairment of the organism and energy metabolism impairment. Therefore, the most important prophylaxis and treatment for hypoxia is to guarantee oxygen supply to the organism so as to maintain healthy working of its energy metabolism, prevent and treat impairment of the histocyte. Clinically, dizziness, encephalalgia, tinnitus, dim sight, limb asthenia, decreasing exercise capacity, mental slowness and memory deterioration, or nausea, emesis, palpitation, brachypnea, polypnea and rapid and weak heart beat are general illnesses of hypoxia. In addition, hypoxia can also cause severe complications including, among others, myocardial infarction, angina pectoris, heart failure, pulmonary edema and cerebral edema, respiratory disorder, injury of optic nerve, injury of cranial nerve and cerebral apoplexy.

Hypoxia can be classified into four types: hypotonic hypoxia, anemic hypoxia, circulatory hypoxia and histogenous hypoxia. Anemic hypoxia and histogenous hypoxia are caused by oxygen impairment, while hypotonic hypoxia and circulatory hypoxia are caused by lack of oxygen supply. Clinically, the co-existence of mixed hypoxia, hypotonic hypoxia and circulatory hypoxia is common.

Hypotonic hypoxia, a common hypoxia in industrial production and daily life, refers to hypoxia caused by lack of oxygen supply to the organism due to obvious decrease of oxygen partial pressure, such as hypoxia caused by external respiratory dysfunction, high altitude hypoxia, aerohypoxia, tunnel hypoxia, diving hypoxia and airtight cabin hypoxia, among which high altitude hypoxia is very common and is the core of hypoxia prophylaxis and treatment.

Tunnel hypoxia refers to hypoxia caused by the fact that the proportion of oxygen in bottom air in the tunnel or cave of a certain depth decreases due to the high proportion of carbon dioxide, leading to decrease of oxygen partial pressure. Diving hypoxia and airtight cabin hypoxia refer to hypoxia caused by the decrease of oxygen partial pressure due to the lower oxygen proportion in the environment. The most common prophylaxis to the said hypoxia is fresh air supplement, oxygen uptake and evacuation from oxygen-lacking area; however, there is not any drug means.

High altitude hypoxia and aerohypoxia refer to hypoxia which occurs, in plateau or high altitude area with an altitude of over 3000 meters, due to low air pressure and accordingly decreased oxygen partial pressure, and reduced difference of oxygen partial pressure in the atmosphere and alveoli with the increase of altitude, directly influencing alveolar gas exchange, oxygen carrying capacity of the blood and release speed of the binding oxygen in the organism, and further leading to lack of oxygen supply to the organism. Acute high altitude stress occurs when people live in the plain go to the plateau of above 3000 m within a short time, or when people live in the plateau go to the plain and then return to the plateau after a period of time. The mild one has the illnesses of encephalalgia, dizziness, palpitation and brachypnea, while the severe one has the illnesses of loss of appetite, nausea, emesis, insomnia, fatigue, hypouresis, abdominal distension and chest distress. Clinically, cyanosis of lips and face, hand and ankle edema are common More severe acute high altitude stress can lead to vasoconstriction of the small pulmonary vein and increase resistance, and then cause pulmonary hypertension and the increase of pulmonary capillary permeability. In addition, hypoxia can also cause lymphatic circulatory disturbance. Therefore, pulmonary edema occurs, and may lead to spasm of small brain vascular and increase the permeability and further cause other acute high altitude stress like brain edema. High altitude stress will be developed into chronic high altitude stress once it lasts for three months. If the symptom of high altitude hypoxia cannot disappear automatically, it will cause people to die due to the necrosis of such vital organs as heart, brain and lung. Traditional non-drug treatments for high altitude hypoxia are high pressure oxygen uptake and evacuation from high altitude area. It is of good efficiency, but cannot be used widely subject to conditions. Adjuvant treatment of drugs is often used for high altitude hypoxia. Clinically, diuretics acetazolamide, corticoid dexamethasone, vasodilator nimodipine, vitamins and aminophylline are used, but their effect is limited. Acetazolamide is most commonly used, but it only works to a certain degree for people who stay in the plateau area for short time. For people who stay in the plateau area for long time, it cannot be taken for a long period since it can easily cause such adverse reactions as electrolyte disturbance, polyuria and dehydration. Other drugs such as hormone also cannot be taken for a long period. In addition, *rhodiola*-contained traditional Chinese medicine preparation which can assist in enhancing the adaptability to hypoxia is also used for hypoxia prophylaxis and treatment. But it works slowly with a limited effect for anti-hypoxia. According to literature (Chinese Invention Patent, Application No. 200310104871.X), supplement of L-carnitine can prevent and treat high altitude stress. Survival time test of anoxic mice under normal pressure and swimming test of mice under low pressure prove that L-carnitine works to some degree for anti-hypoxia under low pressure. L-carnitine can promote the fatty acid metabolism, reduce the accumulation of acid metabolites such as lactic acid and increase energy supply, reduce the content of free fatty acid and acyl fatty acid by promoting fatty acid oxidation, and reduce the damage to cell membrane, increase the stability of cell membrane, especially vital tissue cells like myocardial cells and brain cells and to a certain degree play a role in anti-hypoxia. But fatty acid oxidation needs to consume large amounts of oxygen, so oxygen supply is limited under the circumstance of hypoxia. Therefore, L-carnitine may aggravate hypoxia due to large amounts of oxygen consumption when promoting fatty acid oxidation.

Circulatory hypoxia is also common in clinical practice. Circulatory hypoxia, also known as hypokinetic hypoxia, refers to hypoxia caused by reduced oxygen supply to the tissue due to decreased blood flow. It mainly occurs to patients with heart disease, angina pectoris, cardiac insufficiency, myocardial infarction, heart failure, diseases caused by blood vessel blockage, cerebral apoplexy and arteriovenous atherosclerosis. In clinic practice, drugs such as nitrate, β adrenoceptor antagonist and Ca-antagonist which can change hemodynamics and cerebral vasodilator vinpocetine are often used. The role of the above-mentioned drugs in prophylaxis and treatment of tissue cell impairment of the organism caused by hypoxia is limited and cannot meet the need to prevent and treat circulatory hypoxia. Moreover, trimetazidine which does not change hemodynamics is also used in clinic practice to treat circulatory hypoxia of heart and brain. Trimetazidine, a strong anti-angina drug, is often used in clinic practice to treat coronary insufficiency, stenocardia and previous myocardial infarction. It works slower than nitroglycerin, but its effect can last for longer time. 60%-70% normal myocardial energy (ATP) supply comes from the oxidation of free fatty acid β, 20%-25% the oxidation of glucose, and 5%-10% the glycolysis. Trimetazidine can inhibit fatty acid oxidation, promote glucose oxidation, and work to some degree for anti-myocardial ischemia, but glucose oxidation can only provide 20% energy, far from enough to meet the energy needed to the activities of heart and skeletal muscle. Trimetazidine's inhibition of fatty acid oxidation could cause the accumulation of large numbers of fatty acids, which will damage cell membrane and mitochondria structure, reduce the activity of pyruvate dehydrogenase, and in return inhibit glucose oxidation. Therefore, there are some shortcomings using trimetazidine alone for prophylaxis and treatment of hypoxia.

In conclusion, there is still a gap in developing an ideal antihypoxic drug, which shall first guarantee under the condition of low pressure or low oxygen (hypotonic hypoxia or circulatory hypoxia) the oxygen supply to the organism and its normal energy metabolism, protect impaired tissue cells due to hypoxia, and have no obvious adverse effect for long-term taking. It shall have the features of prophylaxis and treatment. Obviously, there is a lack of such pharmaceutical preparation with the said features and stable quality in the market.

SUMMARY OF INVENTION

The first objective of the present invention is to provide an antihypoxic pharmaceutical composition.

The second objective of the present invention is to provide an antihypoxic pharmaceutical preparation, which can prevent and treat diseases and illnesses caused by hypoxia.

The third objective of the present invention is to provide an antihypoxic method which can be used to prevent and treat diseases caused by hypoxia.

The inventor finds through studies that L-carnitine (in particular) or a derivative or a pharmaceutically acceptable salt thereof which can promote fatty acid oxidation can be used together with or prepared into composition with cerebral vasodilator vinpocetine for anti-hypoxia and the prophylaxis and treatment of diseases and illnesses caused by hypoxia, guaranteeing the supply of oxygen to the organism and normal energy metabolism as well as protection to the impaired tissue cells due to hypoxia. It has the features of prophylaxis and treatment, and can be taken for a long period without obvious adverse effect. As compared to the use of one drug alone, combined use of the said drugs or use of the composition prepared by the said drugs can make a distinct synergistic anti-hypoxia effect, and is suitable for the prophylaxis and treatment of various diseases and illnesses caused by hypoxia.

The inventor also finds through studies that trimetazidine and a pharmaceutically acceptable salt thereof used to treat angina, in particular, trimetazidine hydrochloride, can be used together with or prepared into composition with vinpocetine and L-carnitine or a derivative thereof for anti-hypoxia and the prophylaxis and treatment of diseases and illnesses caused by hypoxia, guaranteeing the supply of oxygen to the organism and normal energy metabolism as well as protection to the impaired tissue cells due to hypoxia. It has the features of prophylaxis and treatment, and can be taken for a long period without obvious adverse effect. As compared to the use of one drug alone, it can make a distinct synergistic anti-hypoxia effect, and is suitable for the prophylaxis and treatment of various diseases and illnesses caused by hypoxia.

"Hypoxia" is a pathological process in which the metabolism, function and morphological structure of the tissue are abnormally changed due to lack of oxygen supply or oxygen impairment. The antihypoxic composition of the present invention is used for prophylaxis and treatment of the abnormal change of metabolism, function and morphological structure of the tissue caused by lack of oxygen supply or oxygen impairment. It is particularly suitable for the prophylaxis and treatment of the abnormal change of metabolism, function and morphological structure of the tissue caused by lack of oxygen supply. Obviously, hypotonic hypoxia or circulatory hypoxia is caused by lack of oxygen supply to the tissue. The antihypoxic composition of the present invention preferably chooses the one for resisting hypotonic hypoxia or circulatory hypoxia. Hypotonic hypoxia, a common hypoxia in industrial production and daily life, refers to hypoxia caused by the lack of oxygen supply due to obvious decrease of oxygen partial pressure, such as hypoxia caused by external respiratory dysfunction, high altitude hypoxia, aerohypoxia, tunnel hypoxia, diving hypoxia and airtight cabin hypoxia, among which high altitude hypoxia is very common. Circulatory hypoxia, also known as hypokinetic hypoxia, is common as well, referring to hypoxia caused by reduced oxygen supply to the tissue due to decreased blood flow. It can be classified into three types as hypoxia caused by blood vessel blockage, hypoxia caused by blood vessel stenosis and hypoxia caused by cardiac insufficiency. It mainly occurs to patients with cardiovascular and cerebrovascular diseases and nerve system diseases, such as shock, cardiac insufficiency, stenocardia, myocardial infarction, diseases caused by blood vessel blockage, vascular atherosclerosis, cerebral infarction, encephalalgia, migraine, injury of optic nerve, and injury of cranial nerve. Hypoxia caused by blood vessel blockage refers to hypoxia which occurs due to the lack of blood supply to the tissue caused by blood vessel blockage by the formation of thrombus. Hypoxia caused by blood vessel stenosis refers to hypoxia which occurs due to the lack of blood supply to the tissue caused by increased blood flow resistance by the arteriovenous atherosclerosis. Hypoxia caused by cardiac insufficiency refers to hypoxia which occurs due to the lack of blood supply to the tissue caused by insufficient heart power and heart pump.

Clinically, dizziness, encephalalgia, tinnitus, dim sight, limb asthenia, decreasing exercise capacity, mental slowness and memory deterioration, or nausea, emesis, palpitation, brachypnea, polypnea and rapid and weak heart beat are general illnesses of hypoxia. In addition, myocardial infarction, heart failure, angina pectoris, pulmonary edema and cerebral edema, shock, respiratory disorder, cerebral apoplexy, injury of optic nerve, injury of cranial nerve are severe diseases caused by hypoxia.

Anti-hypoxia of the present invention is to provide prophylaxis and treatment for the illnesses and diseases caused by hypoxia in clinic practice, especially for general illnesses such as dizziness, encephalalgia, tinnitus, dim sight, limb asthenia, decreasing exercise capacity, mental slowness and memory deterioration, or nausea, emesis, palpitation, brachypnea, polypnea and rapid and weak heart beat, and server diseases such as myocardial infarction, angina pectoris, pulmonary edema and cerebral edema, cerebral apoplexy, shock, respiratory disorder, injury of optic nerve, injury of cranial nerve and cerebral apoplexy.

In conclusion, the present invention creatively develops an antihypoxic pharmaceutical composition.

The pharmaceutical composition of the present invention contains vinpocetine and L-carnitine, or a derivative and a pharmaceutically acceptable salt thereof, with their weight ratio as one of the important technical features. Generally speaking, the weight ratio of vinpocetine and L-carnitine, or a derivative and a pharmaceutically acceptable salt thereof in the pharmaceutical composition of the present invention can be about 1:3-30000, or about 1:33-1800. According to the difference of selected compatible drugs, administration methods and indications, the best weight ratio of vinpocetine and L-carnitine, or a derivative and a pharmaceutically acceptable salt thereof of the present invention can be reached through study.

The pharmaceutical composition of the present invention contains vinpocetine and L-carnitine, with their weight ratio as one of the important technical features. Generally speaking, the weight ratio of vinpocetine and L-carnitine in the pharmaceutical composition of the present invention can be about 1:33-1800, or about 1:300. According to the difference of administration methods and indications, the best weight ratio of vinpocetine and L-carnitine of the present invention can be reached through study.

The pharmaceutical composition of the present invention contains either L-carnitine or a derivative or a pharmaceutically acceptable salt thereof and vinpocetine, or L-carnitine or a derivative or a pharmaceutically acceptable salt thereof, vinpocetine, trimetazidine or a pharmaceutically acceptable salt thereof.

The pharmaceutical composition of the present invention contains vinpocetine, L-carnitine or a derivative or a pharmaceutically acceptable salt thereof, and trimetazidine or a pharmaceutically acceptable salt thereof, with their weight ratio as one of the important technical features. Generally speaking, the weight ratio of vinpocetine, L-carnitine or a derivative and a pharmaceutically acceptable salt thereof, and trimetazidine hydrochloride and a pharmaceutically acceptable salt thereof in the pharmaceutical composition of the present invention can be about 1:3-30000:0.03-60, or about 1:33-1800:0.5-12. The best weight ratio of vinpocetine, L-carnitine or a derivative and a pharmaceutically acceptable salt thereof, and trimetazidine hydrochloride and a pharmaceutically acceptable salt thereof in the pharmaceutical composition of the present invention can be reached through study according to the difference of selected compatible drugs, administration methods and indications.

The pharmaceutical composition of the present invention contains vinpocetine, L-carnitine and trimetazidine hydrochloride, with their weight ratio as one of the important technical features. Generally speaking, the weight ratio of vinpocetine, L-carnitine and trimetazidine hydrochloride can be about 1:33-1800:0.5-12, or about 1:300:2. The best proportion of vinpocetine, L-carnitine and trimetazidine hydrochloride in the pharmaceutical composition of the present invention can be reached through study according to the difference of administration methods and indications.

In the pharmaceutical composition of the present invention, derivatives of L-carnitine include but are not limited to: L-carnitine, acetyl L-carnitine, propionyl L-carnitine and pharmaceutically acceptable salts thereof. L-carnitine, acetyl L-carnitine and pharmaceutically acceptable salts thereof are preferable, L-carnitine in particular.

The pharmaceutically acceptable salts of the present invention include salts formed by L-carnitine or a derivative thereof and trimetazidine with inorganic acids or organic acids, such as hydrochloric acid, hydrobromic acid, hydriodic acid, sulfuric acid, nitric acid, phosphoric acid, acetic acid, maleic acid, fumaric acid, citric acid, oxalic acid, succinic acid, tartaric acid, malic acid, mandelic acid, trifluoroacetic acid, pantothenic acid, methyl sulfonic acid and p-toluene sulfonic acid.

The antihypoxic composition of the present invention can be composition combined by drugs that could improve or promote cardiodynamics or cerebral hemodynamics, such as composition of two or more drugs of nitrate (isosorbide mononitrate, nitroglycerin), β adrenoceptor antagonist (carvedilol), and Ca-antagonist (nifedipine), or composition of one or more drug combinations that can improve or promote cardiodynamics or cerebral hemodynamics with one, two or three drugs such as L-carnitine or a derivative thereof, trimetazidine and a pharmaceutically acceptable salt thereof and vinpocetine.

On the other hand, the present invention provides a pharmaceutical preparation, which contains active ingredient vinpocetine, L-carnitine or a derivative or a pharmaceutically acceptable salt thereof, and other pharmaceutically acceptable auxiliary materials.

The pharmaceutical preparation of the present invention contains active ingredient vinpocetine, L-carnitine or a derivative and a pharmaceutically acceptable salt thereof, and one or more pharmaceutically acceptable carriers. The weight ratio of vinpocetine, and L-carnitine or a derivative and a pharmaceutically acceptable salt thereof can be about 1:3 to about 1:30000, such as about 1:33-1800.

The pharmaceutical preparation of the present invention contains active ingredient vinpocetine and L-carnitine, and one or more pharmaceutically acceptable carriers. The weight ratio of vinpocetine and L-carnitine can be about 1:33 to about 1:1800, such as about 1:300.

The pharmaceutical preparation of the present invention contains active ingredient vinpocetine, L-carnitine or a derivative and a pharmaceutically acceptable salt thereof, trimetazidine and a pharmaceutically acceptable salt thereof, and one or more pharmaceutically acceptable carriers. The weight ratio of vinpocetine, L-carnitine or a derivative or a pharmaceutically acceptable salt thereof, and trimetazidine or a pharmaceutically acceptable salt thereof can be about 1:3-30000:0.03-60, or about 1:33-1800:0.5-33.

The pharmaceutical preparation of the present invention contains active ingredient vinpocetine, L-carnitine, trimetazidine hydrochloride, and one or more pharmaceutically acceptable carriers. The weight ratio of vinpocetine, L-carnitine and trimetazidine hydrochloride can be about 1:15-1500:0.1-25, or about 1:300:2.

The pharmaceutical preparation of the present invention can be taken by oral or parenterally administered. Parenteral administration includes intravenous, intramuscular, peritoneal, subcutaneous, rectal and partial administration.

The pharmaceutical preparation of the present invention can be produced in forms suitable for oral administration, such as tablet, sustained release tablet, pastille, aqueous solution or mixed oil suspension, granule, emulsion, hard or soft capsule or syrup.

The pharmaceutical preparation of the present invention can be packed in a combination, in which the drug can all be oral or injected preparation.

Oral preparation of the present invention can be made according to any known methods for producing oral pharmaceutical composition, and such composition can include one or more substances such as edulcorant, corrective agent, colorant and preservative to make aesthetic and palatable preparations.

Tablet contains active ingredients and pharmaceutically acceptable excipients which can be mixed with active ingredients and are suitable for making tablets. The excipients can be inert diluent such as calcium carbonate, sodium carbonate, lactose, calcium phosphate or sodium phosphate, granulating agent, disintegrant such as microcrystalline cellulose, sodium carboxymethyl cellulose, corn starch or alginate, binder such as starch, gelatin, polyvinylpyrrolidone or gum Arabic, and lubricant such as magnesium stearate, stearic acid or talcum powder.

Tablet can be uncoated or coated with water-soluble taste-masked materials such as hydroxypropyl methyl cellulose or hydroxy propyl cellulose, or time-delay materials such as ethyl cellulose and cellulose acetate butyrate, in virtue of technologies known to the public to mask their unpleasant taste or delay their disintegration and absorption in the gastrointestinal tract, and further keep the drug effect for longer time.

The oral preparation of the present invention can also be provided in forms of hard gelatin capsule, with active ingredient mixed with inert solid diluent such as calcium carbonate, calcium phosphate and kaolin, or soft gelatin capsule, with active ingredient mixed with water-soluble carriers such as polyethylene glycol or oil agents such as peanut oil, liquid paraffin and olive oil.

The water suspension of the present invention contains active substances and excipients or dispersants which can be mixed with active substances and are suitable for making water suspension. The said excipients include suspension such as sodium carboxymethyl cellulose, methyl cellulose, hydroxypropyl methyl cellulose, sodium alginate, polyvinylpyrrolidone, tragacanth gum and gum Arabic. The said dispersants can be natural phospholipid such as lecithin, or condensation product of alkylene oxide and fatty acid such as polyoxyethylene stearate, or condensation product of alkylene oxide and long chain aliphatic alcohol such as seventeen ethylnenoxy cetyl alcohol, or condensation product of alkylene oxide and partial ester derived from fat and hexitol such as polyoxyethylene sorbitan monooleate.

The injection of the present invention is sterile injection powder or crystal containing active substances, and is made through dissolution of crystals by water or such organic solvents as alcohol, methanol, acetone, chloroform, and then drying the solution in normal or freezing temperature.

The injection of the present invention is sterile injection containing active substances, and is made by using water, or ringer solution, sodium chloride solution and/or glucose solution as carrier.

The injection of the present invention can be delivered into patients' blood flow or other drug-deliverable site through partial, fast intramuscular injection or into patients' blood flow through intravenous drip.

The preparations of the present invention can be packed in a combination by combining preparation of L-carnitine or a derivative and a pharmaceutically acceptable salt thereof with that of trimetazidine and a pharmaceutically acceptable salt thereof sold in the market according to certain proportion.

The preparations of the present invention can be packed in a combination by combining preparation of L-carnitine or a derivative and a pharmaceutically acceptable salt thereof with preparation of trimetazidine and a pharmaceutically acceptable salt thereof and that of vinpocetine sold in the market according to certain proportion.

The present invention also provides a method for making pharmaceutical preparation, including the method to mix the said pharmaceutical compositions of the present invention with one or more pharmaceutically acceptable carriers or excipients.

The present invention also provides a method for anti-hypoxia, which gives either 3-ketozcid CoA thiolase inhibitor such as trimetazidine hydrochloride or phosphodiesterase inhibitor such as vinpocetine alone with L-carnitine or a derivative and a pharmaceutically acceptable salt thereof, or both of them with L-carnitine or a derivative and a pharmaceutically acceptable salt thereof one before the other or simultaneously to people who will be exposed in hypoxic environment or those who are suffering diseases caused by hypoxia, or gives pharmaceutical compositions or preparations made from such compositions of the present invention to people who will be exposed in hypoxic environment or those who are suffering diseases caused by hypoxia as treatment and prophylaxis of hypoxia.

Among the preparations of the present invention, the pharmaceutical preparation of L-carnitine and vinpocetine is one of the preferable preparations. For adults of 60 kg, the daily dosage of L-carnitine or a derivative thereof is 10-500 mg/kg; vinpocetine 0.05-0.5 mg/kg.

Among the preparations of the present invention, the pharmaceutical preparation of L-carnitine, vinpocetine, and trimetazidine hydrochloride is one of the preferable preparations. For adults of 60 kg, the daily dosage of L-carnitine or a derivative thereof is 10-500 mg/kg; vinpocetine 0.05-0.5 mg/kg; trimetazidine hydrochloride 0.1-1.5 mg/kg.

EMBODIMENT

The following examples are only used to further explain the present invention, not to limit the scope of the present invention.

Example 1

An Observation of Influence of Intravenously Injected Composition of Vinpocetine and L-Carnitine in Different Dosages on Mice Under the Condition of Normobaric Hypoxia Vinpocetine: 0.75, 2.25, 4.5 mg/kg, the equivalent of daily dosage of about 5, 15, 30 mg human take;

L-carnitine: 150, 450, 1350 mg/kg, the equivalent of daily dosage of about 1, 3, 9 g human take (the highest dosage is the equivalent of about one third to a quarter of the highest clinical injection dosage).

L-carnitine+vinpocetine: setting as 150+0.75, 150+2.25, 150+4.5, 450+0.75, 450+2.25, 450+4.5, 1350+0.75, 1350+2.25, 1350+4.5 mg/kg according to different effect of the two drugs.

Choose 100 male mice with weight of 20±2 g, randomly group them into 10 by weight with each group of 10 mice, and then inject 10 ml/kg preparation to experimental groups, and the same volume of normal saline to control group by tail intravenous injection once a day for consecutive 7 days. One hour after the last injection, put each mouse into a 160 ml wild-mouth bottle, into which 5 g soda lime has been pre-added, and then seal tightly the caps with petroleum jelly. Record survival time of the mice with death as the indicator. [Yue ZHENG, Yang J I, *Animal Models Commonly Used in Researches for Increasing Hypoxia Tolerance and Medicines for Increasing Hypoxia Tolerance, Pharm J Chin PLA*, 2010, 26(2):170-173]. See Table 1 for the results.

TABLE 1

Comparison of Hypoxia Tolerance and Survival Time of Mice under the Condition of Normobaric Hypoxia (n = 10, $\bar{x} \pm S$)

| Group/Dosage (mg/kg) | Survival Time (min) | Prolonged Survival Time (%) |
|---|---|---|
| Control Group | 22.1 ± 4.4 | — |
| L-carnitine 150 + vinpocetine 0.75 | 27.6 ± 3.2* | 24.9 |
| L-carnitine 150 + vinpocetine 2.25 | 29.4 ± 4.6** | 33.0 |
| L-carnitine 150 + vinpocetine 4.5 | 31.7 ± 5.1** | 43.4 |
| L-carnitine 450 + vinpocetine 0.75 | 31.2 ± 2.4** | 41.1 |
| L-carnitine 450 + vinpocetine 2.25 | 33.8 ± 2.8** | 53.8 |
| L-carnitine 450 + vinpocetine 4.5 | 36.9 ± 1.9** | 66.6 |
| L-carnitine 1350 + vinpocetine 0.75 | 33.8 ± 3.7** | 52.9 |
| L-carnitine 1350 + vinpocetine 2.25 | 36.6 ± 6.1** | 65.6 |
| L-carnitine 1350 + vinpocetine 4.5 | 39.1 ± 5.6** | 76.9 |

Remarks: As compared to the control group, *$P < 0.05$, **$P < 0.01$.

It shows that the hypoxia tolerance and survival time of each mouse in groups given preparation can be significantly prolonged, which proves that the composition of L-carnitine and vinpocetine is antihypoxic and can prevent and treat the diseases and illnesses caused by hypoxia. The prolonged survival time is influenced greatly by and is positively associated with the proportion of L-carnitine, and the best proportion of vinpocetine and L-carnitine is 1:300.

Example 2

An Observation of Influence of Intragastrically Administering L-Carnitine and Vinpocetine in Different Dosages on Mice Under the Condition of Normobaric Hypoxia Vinpocetine: 0.75, 1.5, 2.25 mg/kg, the equivalent of daily dosage of about 5, 10, 15 mg human take;

L-carnitine: 150, 300, 450 mg/kg, the equivalent of daily dosage of about 1, 2, 3 g human take.

L-carnitine+vinpocetine: setting as 150+1.5, 300+0.75, 300+1.5, 300+2.25, 450+1.5 mg/kg according to the different effect of the two drugs.

Choose 80 male mice with weight of 20±2 g, randomly group them into 8 by weight with each group of 10 mice, and then administer 20 ml/kg preparation intragastrically to the mice of experimental groups, and the same volume of normal saline to control group once a day for consecutive 7 days. One hour after the last administration, put each mouse into a 160 ml wild-mouth bottle, into which 5 g soda lime has been pre-added, and then seal tightly the caps with petroleum jelly. Record survival time of the mice with death as the indicator. It shows that when the dosage of vinpocetine is 1.5 mg/kg, different weight ratio of L-carnitine and vinpocetine can significantly prolong hypoxia tolerance time of the mice in normal pressure, and the hypoxia tolerance time prolongs as the dosage of L-carnitine increases, and when the dosage of L-carnitine is 300 mg/kg, different weight ratio of L-carnitine and vinpocetine can significantly prolong hypoxia tolerance time of the mice in normal pressure, and the hypoxia tolerance time prolongs as the dosage of vinpocetine increases. See Table 2 for the results.

TABLE 2

Comparison of Hypoxia Tolerance and Survival Time of Mice under the Condition of Normobaric Hypoxia (n = 10, $\bar{x} \pm S$)

| Group/Dosage (mg/kg) | Survival Time (min) | Prolonged Survival Time (%) |
|---|---|---|
| Control Group | 22.6 ± 3.4 | — |
| L-carnitine 150 + vinpocetine 1.5 | 28.5 ± 3.2** | 26.1 |
| L-carnitine 300 + vinpocetine 0.75 | 29.1 ± 4.5** | 28.8 |
| L-carnitine 300 + vinpocetine 1.5 | 31.6 ± 5.4** | 44.2 |
| L-carnitine 300 + vinpocetine 2.25 | 32.8 ± 5.7** | 45.1 |
| L-carnitine 450 + vinpocetine 1.5 | 33.9 ± 4.9** | 50.0 |

Remarks: As compared to the control group, **$P < 0.01$.

It shows that the composition of L-carnitine and vinpocetine is antihypoxic and can prevent and treat the diseases and illnesses caused by hypoxia, and the best weight ratio of vinpocetine and L-carnitine is 1:300.

Example 3

Comparison of Intragastric Administration of L-Carnitine 450 mg/Kg+Vinpocetine 1.5 mg/Kg with that of L-Carnitine or Vinpocetine Alone to Mice Under the Condition of Normobaric Hypoxia Choose 40 male mice with weight of 20±2 g, randomly group them into 4 by weight with each group of 10 mice, and then administer 20 ml/kg preparation intragastrically to the mice of experimental groups, and the same volume of normal saline to control group once a day for consecutive 7 days. One hour after the last administration, put each mouse into a 160 ml wild-mouth bottle, into which 5 g soda lime has been pre-added, and then seal tightly the caps with petroleum jelly. Record survival time of the mice with death as the indicator. See Table 3 for the results.

TABLE 3

Comparison of Hypoxia Tolerance and Survival Time of Mice under the Condition of Normobaric Hypoxia ($n = 10, \bar{x} \pm S$)

| Group/Dosage (mg/kg) | Survival Time (min) | Prolonged Survival Time (%) |
|---|---|---|
| Control Group | 22.5 ± 5.6 | — |
| Vinpocetine 1.5 | 25.1 ± 4.8* | 13.6 |
| L-carnitine 450 | 29.6 ± 3.6** | 31.6 |
| Vinpocetine 1.5 + L-carnitine 450 | 35.2 ± 5.1** | 56.4 |

Remarks: As compared to the control group, *P < 0.05, **P < 0.01.

It shows, as compared to using L-carnitine or vinpocetine alone, that vinpocetine 1.5 mg/kg+L-carnitine 450 mg/kg can significantly prolong hypoxia tolerance time of the mice. The two drugs have synergistic effect, and compound preparation is superior to single preparation.

Example 4

An Observation of Influence of Injecting Vinpocetine, L-Carnitine and Trimetazidine Hydrochloride in Different Weight Ratio on Mice Under the Condition of Normobaric Hypoxia Trimetazidine hydrochloride: 1.12, 2.25, 4.5, 9 mg/kg, the equivalent of daily dosage of 7.5, 15, 30, 60 mg human take.
Vinpocetine: 0.75, 2.25, 4.5 mg/kg, the equivalent of daily dosage of about 5, 15, 30 mg human take;
L-carnitine: 150, 450, 1350 mg/kg, the equivalent of daily dosage of 1, 3, 9 g human take;
Choose 370 male mice with weight of 20±2 g, randomly group them into 37 by weight with each group of 10 mice, and then inject 10 ml/kg preparation to experimental groups, and the same volume of normal saline to control group once a day for consecutive 7 days. One hour after the last injection, put each mouse into a 160 ml wild-mouth bottle, into which 5 g soda lime has been pre-added, and then seal tightly the caps with petroleum jelly. Record survival time of the mice with death as the indicator. See Table 4 for the results.

TABLE 4

Comparison of Hypoxia Tolerance and Survival Time of Mice under the Condition of Normobaric Hypoxia ($n = 10, \bar{x} \pm S$)

| Group/Dosage (mg/kg) | | | Survival Time (min) | Prolonged Survival Time (%) |
|---|---|---|---|---|
| Control Group | | | 22.4 ± 3.2 | — |
| L-carnitine | 150 + vinpocetine | 0.75 + trimetazidine | 33.1 ± 4.6** | 47.1 |
| L-carnitine | 150 + vinpocetine | 0.75 + trimetazidine | 31.5 ± 4.5** | 40.0 |
| L-carnitine | 150 + vinpocetine | 0.75 + trimetazidine | 30.8 ± 5.1** | 36.9 |
| L-carnitine | 150 + vinpocetine | 0.75 + trimetazidine | 29.9 ± 5.1** | 32.9 |
| L-carnitine | 450 + vinpocetine | 0.75 + trimetazidine | 35.6 ± 4.2** | 58.2 |
| L-carnitine | 450 + vinpocetine | 0.75 + trimetazidine | 34.4 ± 4.1** | 52.9 |
| L-carnitine | 450 + vinpocetine | 0.75 + trimetazidine | 32.5 ± 5.1** | 44.4 |
| L-carnitine | 450 + vinpocetine | 0.75 + trimetazidine | 31.2 ± 4.6** | 38.7 |
| L-carnitine | 1350 + vinpocetine | 0.75 + trimetazidine | 36.1 ± 4.9** | 60.4 |
| L-carnitine | 1350 + vinpocetine | 0.75 + trimetazidine | 34.7 ± 5.7** | 54.2 |
| L-carnitine | 1350 + vinpocetine | 0.75 + trimetazidine | 33.2 ± 5.4** | 47.6 |
| L-carnitine | 1350 + vinpocetine | 0.75 + trimetazidine | 32.4 ± 5.2** | 44.0 |
| L-carnitine | 150 + vinpocetine | 2.25 + trimetazidine | 35.1 ± 4.2** | 56.0 |
| L-carnitine | 150 + vinpocetine | 2.25 + trimetazidine | 34.2 ± 4.5** | 52.0 |
| L-carnitine | 150 + vinpocetine | 2.25 + trimetazidine | 32.6 ± 4.6** | 44.9 |
| L-carnitine | 150 + vinpocetine | 2.25 + trimetazidine | 31.4 ± 5.0** | 39.6 |
| L-carnitine | 450 + vinpocetine | 2.25 + trimetazidine | 35.9 ± 4.4** | 59.6 |
| L-carnitine | 450 + vinpocetine | 2.25 + trimetazidine | 34.9 ± 4.7** | 55.1 |
| L-carnitine | 450 + vinpocetine | 2.25 + trimetazidine | 33.6 ± 4.4** | 49.3 |
| L-carnitine | 450 + vinpocetine | 2.25 + trimetazidine | 32.8 ± 4.4** | 45.8 |
| L-carnitine | 1350 + vinpocetine | 2.25 + trimetazidine | 37.4 ± 4.7** | 66.2 |
| L-carnitine | 1350 + vinpocetine | 2.25 + trimetazidine | 36.4 ± 4.6** | 61.8 |
| L-carnitine | 1350 + vinpocetine | 2.25 + trimetazidine | 35.7 ± 4.6** | 58.7 |
| L-carnitine | 1350 + vinpocetine | 2.25 + trimetazidine | 33.9 ± 4.8** | 50.7 |
| L-carnitine | 150 + vinpocetine | 4.5 + trimetazidine | 37.3 ± 4.6** | 65.8 |
| L-carnitine | 150 + vinpocetine | 4.5 + trimetazidine | 36.5 ± 4.5** | 62.2 |
| L-carnitine | 150 + vinpocetine | 4.5 + trimetazidine | 35.3 ± 5.1** | 56.9 |
| L-carnitine | 150 + vinpocetine | 4.5 + trimetazidine | 34.4 ± 5.4** | 52.9 |
| L-carnitine | 450 + vinpocetine | 4.5 + trimetazidine | 39.3 ± 5.2** | 74.7 |
| L-carnitine | 450 + vinpocetine | 4.5 + trimetazidine | 37.5 ± 5.1** | 66.7 |
| L-carnitine | 450 + vinpocetine | 4.5 + trimetazidine | 36.6 ± 4.8** | 62.7 |
| L-carnitine | 450 + vinpocetine | 4.5 + trimetazidine | 35.1 ± 4.6** | 56.0 |
| L-carnitine | 1350 + vinpocetine | 4.5 + trimetazidine | 40.2 ± 4.9** | 78.7 |
| L-carnitine | 1350 + vinpocetine | 4.5 + trimetazidine | 38.9 ± 5.7** | 72.9 |
| L-carnitine | 1350 + vinpocetine | 4.5 + trimetazidine | 37.8 ± 5.4** | 68.0 |
| L-carnitine | 1350 + vinpocetine | 4.5 + trimetazidine | 36.1 ± 5.2** | 60.4 |

Remarks: As compared to the control group, **P < 0.01.

It shows that hypoxia tolerance and survival time of the mice injected with preparation of the composition of vinpocetine, L-carnitine, and trimetazidine hydrochloride in different weight ratio can be significantly prolonged (P<0.01), and the composition is anti-hypoxic and can prevent and treat the diseases and illnesses caused by hypoxia. The best effect is reached when the weight ratio of vinpocetine, L-carnitine and trimetazidine hydrochloride is 1:300:2.

Example 5

The Role of Intragastrically Administering Composition of L-Carnitine and Vinpocetine, and Composition of L-Carnitine, Vinpocetine and Trimetazidine Hydrochloride Alone or Together on Mice Model of Acute Brain Hypoxia Randomly group 70 Kunming male mice into 7 groups: control group, group of L-carnitine 450 mg/kg, group of trimetazidine 9 mg/kg, group of vinpocetine 1.5 mg/kg, group of L-carnitine 450+trimetazidine 9 mg/kg, group of trimetazidine 9+vinpocetine 1.5 mg/kg, and group of L-carnitine 450+trimetazidine 9+vinpocetine 1.5 mg/kg, with each group of 10 mice. Administer 20 mg/kg preparation intragastrically to the mice of experimental groups, and the same volume of normal saline to control group once a day for consecutive 7 days. One hour after the last administration, behead the mice immediately from behind the ear, and stopwatch the breathing time of mice after their decollation. See Table 5 for the results.

TABLE 5

Role of Single Preparation and Compound Preparation to Mice Model of Acute Brain Hypoxia (n = 10, x̄ ± S)

| Group/Dosage (mg/kg) | Breathing Time after Decollation (S) |
| --- | --- |
| Control Group | 17.4 ± 1.8 |
| L-carnitine 450 | 18.6 ± 1.2 |
| Trimetazidine 9 | 18.5 ± 2.1 |
| Vinpocetine 1.5 | 19.5 ± 1.5 |
| L-carnitine 450 + trimetazidine 9 | 23.8 ± 1.3** |
| Trimetazidine 9 + vinpocetine 1.5 | 20.1 ± 1.6* |
| L-carnitine 450 + trimetazidine 9 + vinpocetine 1.5 | 25.4 ± 2.5** |

Remarks: As compared to the control group, *P < 0.05, **P < 0.01.

Biochemical indicator test of brain tissue: After death of the mice, immediately get their brain tissues in ice bath, wash them in ice saline to remove the residual blood, and then add ice anhydrous ethanol according to the proportion of 1:9. Under the condition of ice bath, high-speed homogenate machine (10 s per times, at intervals of 15 s for 4 times) is used to make the brain tissue into 10% cerebral homogenate. Centrifuge the homogenate under the temperature of 4° C. with the speed of 2000 r/min for 5 min to separate the supernatant, and detect the content of glutamic acid (Glu), aspartic acid (Asp), aminobutyric acid (GABA), and glycine (Gly) in the brain tissue of the mice by amino acid analyzer. After brain injury, the content of Glu, Asp, GABA and Gly, etc. (representatives of the excitatory amino acid (EAA)) in the brain is higher. In particular, one of the important mechanisms that could cause the death of secondary brain injury neurons is the excessive release of Glu. An important reason that leads to delayed neuronal death is the cascade of damage due to calcium overload in the neurons, which is caused by the activation of receptor N-methyl-D-aspartate (NMDA) by Glu. The degree to which the mitochondrial function is damaged determines the death method of neurons [Clemens J A, Stephenson D T, Smalsting E B. *Global ischemia activate nuclear. Storke,* 1997, 28:1073-1076]. See Table 6 for the results.

TABLE 6

Influence on the Content of EAA in Brain Tissue (x̄ ± S, n = 10)

| Group/Dosage (mg/kg) | Glu (μmol/L) | Asp (μmol/L) | GABA (μmol/L) | Gly (μmol/L) |
| --- | --- | --- | --- | --- |
| Control Group | 21.15 ± 1.06 | 16.03 ± 2.11 | 4.11 ± 0.78 | 4.96 ± 2.25 |
| L-carnitine 450 | 18.45 ± 1.22 | 15.68 ± 4.23 | 3.71 ± 1.11 | 3.54 ± 1.29 |
| Trimetazidine 9 | 17.02 ± 0.99 | 15.21 ± 2.06 | 3.44 ± 1.12 | 3.49 ± 1.12 |
| Vinpocetine 1.5 | 19.12 ± 2.01 | 15.46 ± 2.21 | 3.15 ± 1.05 | 3.82 ± 1.84 |
| L-carnitine 450 + trimetazidine | 12.54 ± 1.31** | 15.20 ± 1.05 | 3.15 ± 0.68* | 3.25 ± 2.11 |
| Trimetazidine 9 + vinpocetine | 13.45 ± 1.91* | 15.02 ± 3.76 | 3.26 ± 1.55 | 3.65 ± 2.01 |
| L-carnitine 450 + trimetazidine vinpocetine 1.5 | 11.45 ± 1.43** | 14.98 ± 1.48* | 2.64 ± 1.74** | 3.22 ± 1.48* |

Remarks: As compared to the control group, *P < 0.05, **P < 0.01.

Table 5 shows that: After decollation, the breathing time (P<0.01) of the mice in group of L-carnitine 450+trimetazidine 9 mg/kg and group of L-carnitine 450+trimetazidine 9+vinpocetine 1.5 mg/kg significantly prolongs. The composition has synergistic effect and has significant effect in cerebral antihypoxia. Therefore, the composition is proved to work for treatment of diseases caused by lack of blood and oxygen in brain tissue including, among others cerebral apoplexy, sequela of cerebral infarction and cerebral hemorrhage, and cerebral arteriosclerosis.

Table 6 shows that: As compared to single preparation, compound preparation can significantly reduce the content of EAA in brain tissue, and protect the brain tissue from injuries caused by hypoxia. Therefore, the composition is proved to work for treatment of such nerve injuries as optic nerve injury and cranial nerve injury due to lack of blood and oxygen.

Example 6

An Observation of Influence of Intragastrically Administering L-Carnitine and Vinpocetine in Different Dosage Combination on Rats Under the Condition of Hypobaric Hypoxia The equivalent dosages of vinpocetine and L-carnitine for rats calculated following manufacturer's recommendation for dosages human take are respectively:

Vinpocetine: 0.75, 1.5, 2.25 mg/kg, the equivalent of daily dosage of 5, 10, 15 mg human take; L-carnitine: 150, 300, 450 mg/kg, the equivalent of daily dosage of about 1, 2, 3 g human take;

L-carnitine+vinpocetine: setting as 150+1.5, 300+1.5, 450+1.5, 300+2.25, 300+0.75 mg/kg according to the different effect of the two drugs.

Choose 70 Wister rats with weight of 150 g~190 g, randomly group them into 7 groups: normoxic control group: raised in and got from plain area; group of acute hypoxia: put the animals in hypobaric oxygen cabin with cabin oxygen partial pressure of 11.01 Kpa (approximately equals oxygen partial pressure in altitude of 5000 m), expose them in the environment of continuously decreased pressure and oxygen for 3 days, and then put them in hypobaric oxygen cabin with cabin oxygen partial pressure of 13.25 Kpa (approximately equals oxygen partial pressure in altitude of 4000 m), and take samples [Yue ZHENG, Yang J I, *Animal Models Commonly Used in Researches for Increasing Hypoxia Tolerance and Medicines for Increasing Hypoxia Tolerance, Pharm J Chin PLA*, 2010, 26(2):170-173]; group of administration: intragastric administration of 10 ml/kg preparation. Starting from 4 days before putting them into hypobaric oxygen cabin, collect data and take sample for consecutive 7 days in hypobaric oxygen cabin with cabin oxygen partial pressure of 13.25 Kpa (approximately equals oxygen partial pressure in altitude of 4000 m). All animals are free to eat and drink.

Measure hemodynamic parameters: Insert cardiac catheterization into animals of each group within corresponding time respectively from right external jugular vein to pulmonary artery and from left common carotid artery to aorta and left ventricle; record with 4-channel physiology recorder the heart rate (HR), pulmonary artery pressure (PAP), systolic aortic pressure (SAP), diastolic aortic pressure (DAP), left ventricle systolic pressure (LVSP), left ventriclele diastolic pressure (LVEDP), maximum rate of pressure rise of left ventricle ($+dp/dt_{max}$). See Table 7 for the results.

Blood gas analysis: Collect 1 ml blood from aorta, and use heparin to prevent blood from coagulating, and then measure such blood gas indexes as oxygen partial pressure $PaO_2$ and oxygen saturation $SaO_2$. See Table 8 for the results.

TABLE 8

Influence of L-carnitine + Vinpocetine in Different Dosage Combination on Blood Gas Analysis of Rats under the Condition of Simulated Plateau Hypoxia (n = 10, $\bar{x} \pm S$)

| Group | $PaO_2$ (kPa) | $SaO_2$ (%) |
|---|---|---|
| Normoxic control group | 12.2 ± 2.4 | 91.4 ± 6.3 |
| Group of acute hypoxia | 5.5 ± 1.5 | 63.7 ± 13.8 |
| L-carnitine 150 + vinpocetine 1.5 | 6.8 ± 1.6** | 73.5 ± 12.5** |
| L-carnitine 300 + vinpocetine 1.5 | 7.8 ± 1.6** | 77.2 ± 14.8** |
| L-carnitine 450 + vinpocetine 1.5 | 8.3 ± 2.2** | 85.1 ± 9.8** |
| L-carnitine 300 + vinpocetine 2.25 | 10.2 ± 1.9** | 91.2 ± 16.1** |
| L-carnitine 300 + vinpocetine 0.75 | 6.5 ± 1.2** | 71.2 ± 12.3** |

Remarks: As compared to the group of acute hypoxia, **$P < 0.01$.

Measure myocardial injury markers: Collect 2 ml blood from aorta, and measure the activity of lactic dehydrogenase (LDH) and the content of plasma endothelin (ET-1) and atrial natriuretic peptide (ANP). See Table 9 for the results.

TABLE 7

Influence of L-carnitine + Vinpocetine in Different Dosage Combination on Hematology Indexes of Rats under the Condition of Simulated Plateau Hypoxia (n = 10, $\bar{x} \pm S$)

| Group/Dosage (mg/kg) | PAP (kPa) | SAP (kPa) | DAP (kPa) | LVSP (kPa) | $+dp/dt_{max}$ (kPa) | HR (heat/min) |
|---|---|---|---|---|---|---|
| Normoxic control group | 3.5 ± 0.6 | 15.8 ± 1.6 | 10.5 ± 2.8 | 16.9 ± 1.6 | 664 ± 83 | 360 ± 40 |
| Group of acute hypoxia | 5.3 ± 0.7 | 22.9 ± 3.7 | 15.6 ± 3.2 | 25.5 ± 3.0 | 695 ± 72 | 377 ± 50 |
| L-carnitine 150 + vinpocetine 1.5 | 4.8 ± 0.7* | 20.1 ± 2.1* | 13.5 ± 3.2* | 22.0 ± 2.8* | 630 ± 75* | 375 ± 50 |
| L-carnitine 300 + vinpocetine 1.5 | 4.0 ± 0.5** | 17.2 ± 1.8** | 11.5 ± 2.4** | 18.5 ± 1.9** | 515 ± 60** | 370 ± 45 |
| L-carnitine 450 + vinpocetine 1.5 | 3.9 ± 0.7** | 7.6 ± 2.2** | 11.2 ± 2.1** | 18.3 ± 2.4** | 520 ± 45** | 370 ± 45 |
| L-carnitine 300 + vinpocetine 2.25 | 3.5 ± 0.8** | 16.2 ± 3.4** | 10.6 ± 2.7** | 17.4 ± 1.2** | 495 ± 55** | 365 ± 50 |
| L-carnitine 300 + vinpocetine 0.75 | 4.9 ± 0.5* | 20.1 ± 2.9* | 14.0 ± 2.8* | 22.1 ± 3.6* | 660 ± 75* | 375 ± 50 |

Remarks: As compared to the group of acute hypoxia, *$P < 0.05$, *$P < 0.01$.

TABLE 9

Protection of L-carnitine + Trimetazidine Hydrochloride in Different Dosage combination to Myocardial Injury of Rats under the Condition of Simulated Plateau Hypoxia (n = 10, $\bar{x}$ ± S)

| Group | LDH (U/L) | ET-1 (pg/ml) | ANP (pg/ml) |
|---|---|---|---|
| Normoxic control group | 3469.17 ± 236.15 | 188.52 ± 30.05 | 172.13 ± 52.17 |
| Group of acute hypoxia | 4575.25 ± 391.05 | 861.25 ± 58.13 | 431.21 ± 74.24 |
| L-carnitine 150 + vinpocetine | 4011.05 ± 257.48 | 352.57 ± 55.04 | 206.82 ± 58.19* |
| L-carnitine 300 + vinpocetine | 3826.25 ± 352.67 | 336.54 ± 32.51 | 278.45 ± 51.23* |
| L-carnitine 450 + vinpocetine | 3769.32 ± 194.25 | 306.22 ± 56.67 | 254.11 ± 60.15* |
| L-carnitine 300 + vinpocetine | 3652.01 ± 225.36 | 247.14 ± 42.15 | 295.16 ± 51.14* |
| L-carnitine 300 + vinpocetine | 4215.01 ± 321.05 | 355.03 ± 48.12 | 312.03 ± 65.14* |

Remarks: As compared to the group of acute hypoxia, *P < 0.05, **P < 0.01.

Morphological change of the myocardial tissues: After executing the rats, take their hearts and embed them with paraffin, and then cut them into sections of 4 μm, stain them regularly with hematoxylin-eosin (HE), and observe morphological change of the myocardial tissues with optical microscope. It is found that cardiac muscle fibers of the rats in normoxic control group are neatly arranged with plump cells and clear cell nucleus; cardiac muscle fibers of the rats in group of acute hypoxia are disorganized with myocardial cells abnormally shaped and injured into wave and parts of cell eosinophilically stained; morphological change of the myocardial tissues in administration group is improved to different degree; cardiac muscle fibers of the rats in group of L-carnitine 300+vinpocetine 1.5 mg/kg are basically in order with rare eosinophilic staining.

Table 7 shows that: The hemodynamic indexes of the administration groups significantly increase, proving that the composition of this group is antihypoxic and can be used for prophylaxis and treatment of such diseases as cardiac insufficiency, heart failure and shock featured with low hemodynamic indexes.

Table 8 shows that: The oxygen partial pressure and oxygen saturation of arterial blood of the rats in the administration groups significantly increase (P<0.01), proving that the composition of this invention is antihypoxic and can be used for prophylaxis and treatment of high altitude diseases and respiratory hypoxia.

Table 9 shows that: As compared to the normoxic control group, the LDH activity of blood plasma of the rats in group of acute hypoxia significantly increases (P<0.01), and the content of ET-1 and ANP markedly increases (P<0.01). As compared to the group of acute hypoxia, the LDH activity of the administration groups significantly decreases, and the content of ET-1 and ANP markedly decreases (P<0.01). Therefore, it can be found that the compositions of the present invention can significantly decrease the myocardial injury degree under the condition of hypobaric hypoxia, and can protect to a certain degree the myocardial tissues.

The result of the observation of morphological of the myocardial tissues proves that the compositions of the present invention can stabilize the myocardium cell membrane and protect the myocardium cell.

Example 7

An Observation of Protection of Injecting Vinpocetine 1.5+L-Carnitine 450+Trimetazidine Hydrochloride 9 mg/Kg to Rats Under the Condition of Acute Myocardial Hypoxia Narcotize the rats by injecting 45 mg/kg pentobarbital sodium into their abdominal cavities, fix them with their back on the platforms, shave the hair in surgical areas, disinfect the areas with iodine, and cut the trachea and insert the tube. And then open their chests along the third to fourth rib on the left border of sternum, ventilate mechanically, bluntly separate the pericardium and expose the heart. 15 min after the operation, inject the tested drugs intravenously, and then ligate the anterior descending coronary artery at 2 mm below the junction of pulmonic stenosis and left auricle. After that, it can be seen that the myocardial tissue below the ligature is greyish white, and normal myocardium in non-hypoxic area is dark red. The center of greyish white change interval is infarcted area, and the junctional edge of greyish white and dark red is hypoxic area. At 2 min, 30 min and 180 min respectively after ligating the anterior descending coronary artery, put the probe of Laser doppler blood flow meter in the hypoxia area (in other areas, blood flow, which is higher than the limit of instrument, is in a saturated state), adjust the instrument, and when blood flow of myocardial tissues is relatively stable, record the blood flow for 1 min, and take an average value; after the end of record, execute the rats, take the myocardial tissue homogenate in infarcted, hypoxic and non-hypoxic areas, and at 2 min, 30 min and 3 h after myocardial ischemia, measure the blood flow of the myocardial tissues and the content of glucose, adenosine triphosphate, 6-phosphofructokinase, pyruvate dehydrogenase and free fatty acids in the myocardial tissues respectively. Centrifuge the said homogenate in line with the instruction of the detection kit at the speed of 4000 rpm for 10 min. Then, measure the content of glucose in the supernate with semiautomatic biochemistry analyzer, measure 6-phosphofructokinase (6-PFK) and pyruvate dehydrogenase (PDH) with Elisa kit, and measure free fatty acids and ATP with spectrophotometer. See Table 10-12 for the results.

Influence of Vinpocetine 1.5+L-carnitine 450+Trimetazidine Hydrochloride 9 mg/kg on the Energy Metabolism of Myocardial Tissue Glucose: At 2 min, 30 min and 3 h after acute myocardial hypoxia, the content of glucose in myocardial tissues of non-hypoxic area has no obvious change; in myocardial tissues of hypoxic and infarcted area, the content of glucose should significantly reduce due to disorders and increased glycolysis, but the detection results do not come out that way after 30 min and 3 h of hypoxia. So, it is of no statistic significance to compare with the control group given normal saline (P<0.05).

ATP: As compared to the control group given normal saline, the results of treatment groups after 2 min, 30 min and 3 h of myocardial hypoxia show that the content of ATP in the myocardial tissues of infarcted area significantly increases after 2 min of myocardial hypoxia (P<0.01), which is consistent with the increased content of glucose within a short time after myocardial hypoxia; after 30 min, the content of ATP in the myocardial tissues of non-hypoxic area significantly reduces (P<0.001); after 3 h, the content of ATP of control group given normal saline in non-hypoxic area significantly reduces, but that of treatment group significantly increases. It can be found from the content of ATP of the treatment group in the said three areas of the myocardium, the content of ATP in non-hypoxic area increases over time (563 after 2 min, 406 after 30 min, 807 after 3 h). The content of ATP in hypoxic area has no obvious decrease (741, 698, 607). The content of ATP in hypoxic area has the tendency to reduce over time (683, 477, 461), but it shows no statistically significant difference.

6-phosphofructokinase (6-PFK) is a major rate-limiting enzyme, catalyzing 6-fructose phosphate into fructose-1,6-diphosphate in non-equilibrium glycolysis reaction, and its increased content means the activity of glycolytic pathway. The result of this experiment shows, as compared to the control group given normal saline, that the content of 6-PFK in groups given the drug reduces within short time after administration of the drug, but increases significantly from the time of 30 min to 3 h (P<0.05), which proves that the glycolysis is very active after 2 min of the administration.

Pyruvate dehydrogenase (PDH): PDH is a major enzyme that can make pyruvic acid into acetyl coenzyme A with aerobic oxidation. Its increased activity means the aerobic oxidation is enhanced. The results of the experiment show that, in non-hypoxic, hypoxic and infarcted areas of the myocardium, the content of PDH of the administration groups is significantly lower than that of the control group within 2 min after the ligation of coronary artery. But after 2 min, the content of PDH gradually increases, and after 3 h, the content of PDH in non-hypoxic, hypoxic and infarcted areas significantly increases, which is obviously different from that of control group given normal saline.

Free fatty acids (FFA): after 2 min of the administration, the content of free fatty acids in non-hypoxic, hypoxic and infarcted areas increases as compared to that of group given normal saline, but the increase shows no statistically significant difference.

Blood flow in infarcted area of the myocardium: As compared to the group given normal saline, the blood flow in infarcted area of the myocardial tissues at different time increases after injecting trimetazidine hydrochloride 9+vinpocetine 1.5+L-carnitine 450 mg/kg into rat models of acute myocardial hypoxia, but the increase shows no statistically significant difference.

The result shows that the composition can optimize the energy supply to anoxic myocardial tissues, which proves that it can be used for prophylaxis and treatment of severe ischemic cardiomyopathy such as myocardial infarction.

TABLE 10

Influence of Compound Preparation L-carnitine on Energy Metabolism and Blood Flow of the Myocardium after 2 min of Myocardial Ischemia

| | Non-hypoxic Area | | Hypoxic Area | | Infarcted Area | |
| --- | --- | --- | --- | --- | --- | --- |
| | Group Given Normal Saline | Treatment Group | Group Given Normal Saline | Treatment Group | Group Given Normal Saline | Treatment Group |
| G.S | 0.44 ± 0.15 | 0.45 ± 0.14 | 0.37 ± 0.03 | 0.31 ± 0.07 | 0.34 ± 0.16 | 0.41 ± 0.29 |
| ATP | 747 ± 345 | 563 ± 260 | 879 ± 210 | 741 ± 211 | 351 ± 117 | 683 ± 273** |
| 6-PFK | 4.06 ± 0.99 | 3.01 ± 0.21* | 4.47 ± 1.54 | 2.79 ± 0.21** | 4.54 ± 0.51 | 3.31 ± 0.51** |
| PDH | 1.76 ± 0.71 | 1.00 ± 0.09* | 1.78 ± 0.61 | 1.14 ± 0.14* | 1.88 ± 0.39 | 1.36 ± 0.24** |
| FFA | 226 ± 14.0 | 237 ± 16.2 | 312 ± 30.9 | 347 ± 32.3 | 260 ± 65.9 | 256 ± 28.9 |
| Blood Flow | | | | | 836 ± 19.3 | 852 ± 21.6 |

As compared to the group given normal saline
*P < 0.05
**P < 0.01

TABLE 11

Influence of Compound Preparation L-carnitine on Energy Metabolism and Blood Flow of the Myocardium after 30 min of Myocardial Ischemia

| | Non-hypoxic Area | | Hypoxic Area | | Infarcted Area | |
| --- | --- | --- | --- | --- | --- | --- |
| | Group Given Normal Saline | Treatment Group | Group Given Normal Saline | Treatment Group | Group Given Normal Saline | Treatment Group |
| G.S | 0.45 ± 0.12 | 0.48 ± 0.13 | 0.62 ± 0.24 | 0.53 ± 0.12 | 0.43 ± 0.12 | 0.36 ± 0.07 |
| ATP | 966 ± 313 | 406 ± 65.7*** | 579 ± 197 | 698 ± 146 | 580 ± 207 | 477 ± 245 |
| 6-PFK | 3.07 ± 0.09 | 2.73 ± 0.32* | 3.66 ± 0.66 | 3.10 ± 0.41 | 3.89 ± 0.64 | 4.03 ± 0.70 |
| PDH | 1.06 ± 0.09 | 1.16 ± 0.15 | 1.17 ± 0.28 | 1.08 ± 0.17 | 1.56 ± 0.23 | 1.64 ± 0.28 |
| FFA | 256 ± 17.9 | 275 ± 39.1 | 246 ± 39.4 | 250 ± 26.4 | 261 ± 90.1 | 246 ± 80.8 |
| Blood Flow | | | | | 818 ± 36.9 | 832 ± 38.6 |

As compared to the group given normal saline,
*P < 0.05
**P < 0.01
***P < 0.001

TABLE 12

Influence of Compound Preparation L-carnitine on Energy Metabolism
and Blood Flow of the Myocardium after 3 h of Myocardial Ischemia

| | Non-hypoxic Area | | Hypoxic Area | | Infarcted Area | |
|---|---|---|---|---|---|---|
| | Group Given Normal Saline | Treatment Group | Group Given Normal Saline | Treatment Group | Group Given Normal Saline | Treatment Group |
| G.S | 0.42 ± 0.10 | 0.44 ± 0.10 | 0.83 ± 0.21 | 0.93 ± 0.14 | 0.85 ± 0.15 | 0.63 ± 0.22* |
| ATP | 237 ± 125 | 807 ± 469** | 917 ± 320 | 607 ± 228 | 385 ± 196 | 461 ± 286 |
| 6-PFK | 2.88 ± 0.44 | 3.91 ± 0.66** | 3.42 ± 0.89 | 4.29 ± 0.90* | 3.99 ± 0.81 | 5.21 ± 1.28* |
| PDH | 1.10 ± 0.32 | 1.50 ± 0.26** | 1.15 ± 0.18 | 1.47 ± 0.39* | 1.65 ± 0.33 | 2.02 ± 0.43 |
| FFA | 270 ± 32.9 | 315 ± 45.7 | 258 ± 18.4 | 274 ± 21.5 | 198 ± 28.5 | 211 ± 41.2 |
| Blood Flow | | | | | 859 ± 17.7 | 870 ± 21.7 |

As compared to the group given normal saline,
*P < 0.05
**P < 0.01
***P < 0.001

Example 8

Pharmaceutical Preparation of Composition of L-Carnitine and Vinpocetine in Different Dosages In the present invention, combination of L-carnitine and vinpocetine is taken for example. Various pharmaceutical preparations containing L-carnitine and vinpocetine in different dosages can be made according to the following data L-carnitine 100 mg-30000 mg per day; vinpocetine 1 mg-30 mg per day Set the proportion as 30 g: 1 mg to 0.1 g:30 mg

| Vinpocetine:L-carnitine | Vinpocetine (weight):L-carnitine (weight) |
|---|---|
| 1:30000 | 33.3 mg:1000 g |
| 1:10000 | 100 mg:1000 g |
| 1:1800 | 1 g:1800 g |
| 1:1000 | 1 g:1000 g |
| 1:500 | 1 g:500 g |
| 1:300 | 1 g:300 g |
| 1:100 | 1 g:100 g |
| 1:66 | 1 g:66 g |
| 1:10 | 1 g:10 g |
| 1:3 | 1 g:3 g |

1:30000 333 mg:1000 g

Example

Compound Preparation (Vinpocetine+L-Carnitine) Oral Liquid

| Formulation: L-carnitine | 1000 g |
|---|---|
| Vinpocetine | 0.0333 g |
| Distilled water | Add to 10000 ml |

Process: Take L-carnitine and vinpocetine, dissolve them with 3000 ml distilled water, and then add distilled water to 10000 ml.

1:10000 100 mg:1000 g

Example

Compound Preparation (Vinpocetine+L-Carnitine) Oral Liquid

| Formulation: L-carnitine | 1000 g |
|---|---|
| Vinpocetine | 0.1 g |
| Distilled water | Add to 10000 ml |

Process: Take L-carnitine and vinpocetine, dissolve them with 3000 ml distilled water, and then add distilled water to 10000 ml.

1:1800 1 g:1800 g

Example

Compound Preparation (Vinpocetine+L-Carnitine) Syrup

| Formulation: L-carnitine | 1800 g |
|---|---|
| Vinpocetine | 1 g |
| Distilled water | 150 ml |
| Simple syrup | Add to 10000 ml |

Process: Take L-carnitine and vinpocetine, add distilled water, and then add simple syrup to 10000 ml 1:1000 1 g:1000 g

Example

Compound Preparation (Vinpocetine+L-Carnitine) Emulsion

| Formulation: L-carnitine | 1000 g |
|---|---|
| Vinpocetine | 1 g |
| Arabic gum powder | 125 g |
| Tragacanth powder | 7 g |
| Saccharin sodium | 0.1 g |
| Volatile almond oil | 1 ml |
| Ethylparaben | 0.5 g |
| Distilled water | Add to 1000 ml |

Process: Uniformly grind Arabic gum, L-carnitine and vinpocetine, first add 250 ml distilled water, grind in one direction to make them into preliminary emulsion, and then add aqueous solution of saccharin sodium, volatile almond oil, ethylparaben solution, slowly add tragacanth mucilage and the rest distilled water, and stir them uniformly.

1:500 1 g:500 g

Example

Compound Preparation (L-Carnitine+Vinpocetine) Injection

| Formulation: L-carnitine | 500 g |
|---|---|
| Vinpocetine | 1 g |
| Edetate disodium | 0.5 g |
| Hydrochloric acid | 20 g |
| Water for injection | Add to 1000 ml |

Process: Add 80% of the formulation water for injection in the vessel, then dissolve L-carnitine and vinpocetine into the water, add prepared solution of edetate disodium and hydrochloric acid, and stir them to be uniform. Adjust the PH value of the solution between 6.0 and 6.2, then add the rest water for injection, and decolorize the solution with 0.1% active carbon. After that, filtrate the solution with sintered glass filter and membrane filter, embed in nitrogen atmosphere and sterilize in 100° C. circulating steam for 15 min.

1:300 1 g:300 g

Example

Compound Preparation (L-Carnitine+Vinpocetine) Transfusion

| Formulation: L-carnitine | 300 g |
|---|---|
| Vinpocetine | 1 g |
| Edetate disodium | 5 g |
| Hydrochloric acid | 200 g |
| Water for injection | Add to 10000 ml |

Process: Take about 8000 ml hot water for injection, put L-carnitine and vinpocetine in line with the formulation into it and stir to dissolve them completely, add antioxygen, and adjust the PH value to about 6.0 with 10% hydrochloric acid. After that, add defined amount of water for injection, decolorize the solution with 0.15% active carbon, filtrate the solution to be clear and embed the solution into a 100 ml infusion bottle. And then aerate nitrogen, stopper the bottle and roll the lid, and sterilize in 100° C. for 30 min.

1:66 1 g:66 g

Example

Compound Preparation (Vinpocetine+L-Carnitine) Transfusion

| Formulation: L-carnitine | 660 g |
|---|---|
| Vinpocetine | 10 g |
| Edetate disodium | 5 g |
| Hydrochloric acid | 200 g |
| Water for injection | Add to 10000 ml |

Process: Take about 8000 ml hot water for injection, put L-carnitine and vinpocetine in line with the formulation into it and stir to dissolve them completely, add antioxygen, and adjust the PH value to about 6.0 with 10% hydrochloric acid. After that, add appropriate water for injection, decolorize the solution with 0.15% active carbon, filtrate the solution to be clear and embed the solution into a 100 ml infusion bottle. And then aerate nitrogen, stopper the bottle and roll the lid, and sterilize under the temperature of 100° C. for 30 min.

1:10 1 g:10 g

Example

Compound Preparation (L-Carnitine+Vinpocetine) Tablets

| Formulation: L-carnitine | 1000 g |
|---|---|
| Vinpocetine | 100 g |
| Lactose | 1500 g |
| Starch | 500 g |
| 10% starch slurry | 200 g |
| Dry starch | 20 g |
| Magnesium stearate | 15 g |
| Make 10000 tablets | |

Process: Screen L-carnitine and vinpocetine through 80 mesh sieve, mix them uniformly with starch and lactose, and add starch slurry to make them into soft material. And then make particles through 14 mesh sieve, dry the particles under the temperature of 70° C.~80° C., rearrange the particles through 12 mesh sieve, and mix them uniformly with dry starch and magnesium stearate, and make tablets.

1:10 1 g:10 g

Example

Compound Preparation (L-Carnitine+Vinpocetine) Sustained Release Tablets

| Formulation: L-carnitine | 2000 g |
|---|---|
| Vinpocetine | 200 g |
| Citric acid | 10 g |
| HPMC (K4M) | 160 g |
| Lactose | 180 g |
| Magnesium stearate | 2 mg |
| Make 10000 tablets | |

Process: Mix L-carnitine, vinpocetine, HPMC and lactose uniformly, dissolve citric acid into ethanol to make soft material as humectant, make particles, dry and rearrange the particles, and mix the particles uniformly with magnesium stearate and make tablets.

1:3 1 g:3 g

Example

Compound Preparation (L-Carnitine+Vinpocetine) Soft Capsule

| Formulation: L-carnitine | In 3000 portions |
|---|---|
| Vinpocetine | In 1000 portions |
| Gelatin | In 1000 portions |
| Glycerin | In 55-66 portions |
| Water | In 1200 portions |
| Oleum morrhuae or refined edible vegetable oil | Defined amount |

Process: Take L-carnitine and vinpocetine, dissolve them into oleum morrhuae or refined edible vegetable oil (remove solid fat under the temperature of about 0° C.) and adjust concentration of the solution to make each soft capsule contain 90%~120% vitamin L-carnitine, above 85% vitamin D as labeled. Put the solution aside, take glycerin and water, heat them to the temperature of 70° C.~80° C., and add gelatin, stir and dissolve the gelatin, and then incubate for 1~2 hours. After that, remove the floating foam, filtrate and add into pill dropping machine to make soft capsules. And then collect condensed soft capsules with liquid paraffin as the coolant, wipe the adhesive coolant with gauze, and blow the soft capsules with cold wind under ambient temperature for 4 hours. Then dry the soft capsules under the temperature of 25~35° C. for 4 hours, wash them with petroleum ether for two times (each for 3~5 min) to remove the external liquid paraffin, and wash them again with 95% ethanol and dry them under the temperature of 30~35° C. for 2 hours, filtrate, check and package the soft capsules.

1:3 1 g:3 g

Example

Compound Preparation (Vinpocetine+L-Carnitine) Suppository

| Formulation: L-carnitine | 300 g |
|---|---|
| Vinpocetine | 100 g |
| Ethylparaben | 0.5 g |
| 50% ethanol | 100 ml |
| Polysorbate 80 | 100 ml |
| Glycerinated gelatin | Add to 3000 g |
| Make 2000 suppositories | |

Process: Take L-carnitine and vinpocetine, add into ethanol and boil to completely dissolution, add ethylparaben and stir, and add defined amount of glycerin and stir uniformly, and then slowly add the solution into glycerinated gelatin substrate to preserve heat for later use. Add polysorbate and stir uniformly, and then slowly stir the solution and add into the said glycerinated gelatin substrate, stir well and preserve the heat at 55° C., and affuse into the membrane, and cool them down.

Example 9

Pharmaceutical Preparation Containing L-Carnitine, Vinpocetine and Trimetazidine Hydrochloride L-carnitine:vinpocetine:trimetazidine hydrochloride (300 mg:1 mg:2 mg)

Example

Compound Preparation L-Carnitine Tablets

| Formulation: L-carnitine | 300 g |
|---|---|
| Vinpocetine | 1 g |
| Trimetazidine hydrochloride | 2 g |
| Lactose | 150 g |
| Starch | 50 g |
| 10% starch slurry | 100 g |
| Dry starch | 10 g |
| Magnesium stearate | 5 g |
| Make 1000 tablets | |

Process: Screen L-carnitine, vinpocetine and trimetazidine hydrochloride through 80 mesh sieve, mix them uniformly with starch and lactose, and add starch slurry to make them into soft material. And then make particles through 14 mesh sieve, dry the particles under the temperature of 70° C.~80° C., rearrange the particles through 12 mesh sieve, and mix them uniformly with dry starch and magnesium stearate, and make tablets.

Example 10

Pharmaceutical Preparation Containing L-Carnitine and Vinpocetine According to Specifications for Suppository, L-Carnitine:Vinpocetine (300 mg:0.25 mg)

Example

Compound Preparation (L-Carnitine+Vinpocetine) Suppository

| Formulation: L-carnitine | 300 g |
|---|---|
| Vinpocetine | 0.25 g |
| Ethylparaben | 0.5 g |
| 50% ethanol | 100 ml |
| Polysorbate 80 | 100 ml |
| Glycerinated gelatin | Add to 3000 g |
| Make 1000 suppositories | |

Process: Take L-carnitine and vinpocetine, add into ethanol and boil to completely dissolution, add ethylparaben and stir, and add defined amount of glycerin and stir uniformly, and then slowly add the solution into glycerinated gelatin substrate to preserve heat for later use. Add polysorbate and stir uniformly, and then slowly stir the solution and add it into the said glycerinated gelatin substrate, stir well and preserve the heat at 55° C., and affuse into the membrane, and cool them down.

Example 11

Pharmaceutical Preparation Containing L-Carnitine, Vinpocetine and Trimetazidine Hydrochloride According to specifications for tablets, L-carnitine: trimetazidine hydrochloride: vinpocetine (500 mg:20 mg:10 mg).

Example

Compound Preparation (L-Carnitine+Trimetazidine Hydrochloride+Vinpocetine) Tablets

| Formulation: L-carnitine | 500 g |
|---|---|
| Trimetazidine hydrochloride | 20 g |
| Vinpocetine | 10 g |
| Lactose | 150 g |
| Starch | 50 g |
| 10% starch slurry | 100 g |
| Dry starch | 10 g |
| Magnesium stearate | 5 g |
| Make 1000 tablets | |

Process: Screen L-carnitine, trimetazidine hydrochloride and vinpocetine through 80 mesh sieve, mix them uniformly with starch and lactose, and add starch slurry to make them into soft material. And then make particles through 14 mesh sieve, dry the particles under the temperature of 70° C.~80° C., rearrange the particles through 12 mesh sieve, and mix them uniformly with dry starch and magnesium stearate, and make tablets.

Example 12

Compound Preparation (L-Carnitine+Trimetazidine Hydrochloride+Vinpocetine) Tablets

| Formulation: L-carnitine | 1000 g |
|---|---|
| Trimetazidine hydrochloride | 5 g |
| Vinpocetine | 5 g |
| Lactose | 200 g |
| Starch | 100 g |
| 10% starch slurry | 100 g |
| Dry starch | 20 g |
| Magnesium stearate | 15 g |
| Make 2000 tablets | |

Process: Screen L-carnitine, trimetazidine hydrochloride and vinpocetine through 80 mesh sieve, mix them uniformly with starch and lactose, and add starch slurry to make them into soft material. And then make particles through 14 mesh sieve, dry the particles under the temperature of 70° C.~80° C., rearrange the particles through 12 mesh sieve, and mix them uniformly with dry starch and magnesium stearate, and make tablets.

Example 13

Combined Packaging of L-Carnitine, Trimetazidine Hydrochloride and Vinpocetine Preparations Make or purchase L-carnitine, trimetazidine hydrochloride and vinpocetine preparations separately, as is shown in Table 13.

TABLE 13

L-carnitine and Trimetazidine Hydrochloride Preparations in Different Specifications

| L-carnitine preparation | Trimetazidine hydrochloride preparation | Vinpocetine preparation |
|---|---|---|
| Injection 0.5 g | Trimetazidine hydrochloride tablet 2 mg | Injection 5 mg |
| Injection 1 g | Trimetazidine hydrochloride tablet 3 mg | Injection 10 mg |
| Injection 2 g | Trimetazidine hydrochloride tablet 5 mg | Injection 20 mg |
| Oral tablet 0.25 g | Trimetazidine hydrochloride tablet 10 mg | Injection 30 mg |
| Oral tablet 0.333 g | Trimetazidine hydrochloride tablet 15 mg | Oral tablet 5 mg |
| Oral tablet 0.5 g | Trimetazidine hydrochloride coated tablet 20 mg | Oral tablet 10 mg |
| Oral tablet 1 g | Trimetazidine hydrochloride sustained release tablet 35 mg | Oral tablet 15 mg |
| Oral liquid 2.5 ml:0.25 g | Trimetazidine hydrochloride injection 2 ml:5 mg | Sustained release tablet 10 mg |
| Oral liquid 5 ml:0.5 g | Trimetazidine hydrochloride injection 5 ml:10 mg | Sustained release tablet 15 mg |
| Oral liquid 10 ml:1 g | | |
| Oral liquid 50 ml:5 g | | |
| Oral liquid 100 ml:10 g | | |
| Oral liquid 500 ml:50 g | | |

Pack two or all of the said three preparations randomly in a combination. The preparation number of each combination can be determined according to clinical needs.

What is claimed is:

1. An antihypoxic pharmaceutical composition, comprising:
vinpocetine;
a carnitine component selected from the group consisting of L-carnitine, acetyl-L-carnitine, propionyl-L-carnitine, and pharmaceutically acceptable salts of the foregoing; and
a trimetazine component selected from the group consisting of trimetazine and pharmaceutically acceptable salts thereof;
wherein the weight ratio of vinpocetine to the carnitine component is within the range of 1:3-30000, and wherein the weight ratio of the carnitine component to the trimetazine component is within the range of 1:3-30000:0.03-60.

2. The pharmaceutical composition as described in claim 1, wherein the pharmaceutically acceptable salts of the carnitine component comprise salts formed with an acid selected from the group consisting of hydrochloric acid, hydrobromic acid, hydriodic acid, sulfuric acid, nitric acid, phosphoric acid, acetic acid, maleic acid, fumaric acid, citric acid, oxalic acid, succinic acid, tartaric acid, malic acid, mandelic acid, trifluoroacetic acid, pantothenic acid, methyl sulfonic acid and p-toluene sulfonic acid.

3. The pharmaceutical composition as described in claim 1, wherein the weight ratio of vinpocetine to the carnitine component is within the range of 1:33-1800.

4. The pharmaceutical composition as described in claim 3, wherein the carnitine component is L-carnitine, and wherein the weight ratio of vinpocetine to vinpocetine and L-carnitine is within the range of 1:33-1800.

5. The pharmaceutical composition as described in claim 4, that the composition comprises vinpocetine and L-carnitine, wherein the weight ratio of vinpocetine to L-carnitine is within the range of 1:66-600.

6. The pharmaceutical composition as described in claim 5, wherein the weight ratio of vinpocetine to L-carnitine is 1:300.

7. The pharmaceutical composition as described in claim 1, wherein the weight ratios of vinpocetine, the carnitine component and the trimetazidine component are within the ranges of 1:33-1800:0.5-12.

8. The pharmaceutical composition as described in claim 7, wherein the trimetazidine component is trimetazidine hydrochloride, and wherein the weight ratios of vinpocetine, L-carnitine and trimetazidine hydrochloride are within the ranges of 1:300:2.

9. A pharmaceutical preparation, wherein the preparation is prepared with the ingredients of the pharmaceutical composition of claim 1 as active ingredients, and with at least one pharmaceutically acceptable carrier.

10. The pharmaceutical preparation as described in claim 9, wherein the pharmaceutical preparation is in a form selected from the group consisting of oral administration forms, injection administration forms and topical administration forms.

11. The pharmaceutical preparation as described in claim 10, wherein the oral administration form is selected from the group consisting of tablets, sustained release tablets, granules, hard capsules, soft capsules, syrups, solutions and emulsions.

12. The pharmaceutical preparation as described in claim 10, wherein the injection administration form is sterilely injected in a form selected from the group consisting of aqueous solutions, oil-in-water microemulsions and powders.

13. The pharmaceutical preparation as described in claim 10, wherein the topical administration form is selected from the group consisting of patches, suppositories, creams, ointments, gels, solutions and suspensions.

14. The pharmaceutical preparation as described in claim 9, wherein the active ingredients and at least one carrier are combined within a package.

15. A method for treating a patient exhibiting anti-hypoxia, prophylaxis, or diseases or illnesses caused by hypoxia, comprising:
administering the composition of claim 1 to the patient.

16. The method as described in claim 15, wherein the hypoxia is selected from the group consisting of hypotonic hypoxia and circulatory hypoxia.

17. The method as described in claim 16, wherein the hypotonic hypoxia is selected from the group consisting of high altitude hypoxia, tunnel hypoxia, aerohypoxia, diving hypoxia and airtight cabin hypoxia, and wherein the circulatory hypoxia is selected from the group consisting of hypoxia caused by blood vessel blockage, hypoxia caused by blood vessel stenosis and hypoxia caused by cardiac insufficiency.

18. The method as described in claim 15, wherein the diseases and illnesses caused by hypoxia are selected from the group consisting of dizziness, encephalalgia, tinnitus, dim sight, limb asthenia, decreasing exercise capacity, mental slowness, memory deterioration, nausea, emesis, palpitation, brachypnea, polypnea, rapid and weak heartbeat, high altitude stress, myocardial infarction, angina pectoris, cardiac insufficiency, heart failure, shock, respiratory hypoxia, optic nerve injury, cranial nerve injury, cerebral apoplexy, sequela of cerebral infarction and cerebral hemorrhage, and cerebral arteriosclerosis.

19. The method as described in claim 15, wherein the composition is in a form selected from the group consisting of oral administration forms, injection administration forms and topical administration forms.

20. The method as described in claim 15, wherein the patient is an adult, and wherein the composition is administered in daily dosages of: carnitine component: 10-500 mg/kg; vinpocetine: 0.05-0.5 mg/kg; trimetazidine component: 0.1-1.5 mg/kg.

21. An antihypoxic pharmaceutical composition, comprising:
vinpocetine; and
a carnitine component selected from the group consisting of L-carnitine, acetyl-L-carnitine, propionyl-L-carnitine, and pharmaceutically acceptable salts of the foregoing;
wherein the weight ratio of vinpocetine to the carnitine component is within the range of 1:3-30000, wherein the pharmaceutical composition includes said vinpocetine and said carnitine component as active ingredients, and further includes at least one pharmaceutically acceptable carrier, and wherein the pharmaceutical composition is in an injection administration form in which it is sterilely injected in a form selected from the group consisting of water solutions, oil-in-water microemulsions and powders.

22. An antihypoxic pharmaceutical composition, comprising:
vinpocetine; and
a carnitine component selected from the group consisting of L-carnitine, acetyl-L-carnitine, propionyl-L-carnitine, and pharmaceutically acceptable salts of the foregoing;

wherein the weight ratio of said vinpocetine to said carnitine component is within the range of 1:3-30000, wherein the composition includes said vinpocetine and said carnitine component as active ingredients, and further includes at least one pharmaceutically acceptable carrier, and wherein the pharmaceutical preparation is in a topical administration form selected from the group consisting of patches, suppositories, creams, ointments, gels, solutions and suspensions.

\* \* \* \* \*